United States Patent
Yakushi et al.

(10) Patent No.: US 6,199,361 B1
(45) Date of Patent: Mar. 13, 2001

(54) FALSE TWIST TEXTURING MACHINE

(75) Inventors: Hiroshi Yakushi, Mukou; Shinichiro Morimoto, Nagaokakyo, both of (JP)

(73) Assignee: Murata Kikai Kabushiki Kaisha, Kyoto (JP)

( * ) Notice: Subject to any disclaimer, the term of this patent is extended or adjusted under 35 U.S.C. 154(b) by 0 days.

(21) Appl. No.: 09/186,152

(22) Filed: Nov. 5, 1998

(30) Foreign Application Priority Data

Feb. 26, 1998 (JP) .................................................. 10-045010

(51) Int. Cl.⁷ ...................................................... D02G 1/04
(52) U.S. Cl. .............................. 57/332; 57/58.86; 57/105; 57/238; 57/244; 57/252; 57/264; 57/284; 57/285; 57/332; 57/334; 57/336; 57/341
(58) Field of Search ................................. 57/58.86, 105, 57/238, 244, 252, 264, 284, 285, 332, 334, 336, 341

(56) References Cited

U.S. PATENT DOCUMENTS

| | | | |
|---|---|---|---|
| 4,334,401 | * | 6/1982 | Bahia ........................................ 57/6 |
| 4,445,322 | * | 5/1984 | Satterfield ............................... 57/264 |
| 4,720,702 | * | 1/1988 | Martens ................................. 340/677 |
| 5,136,835 | * | 8/1992 | Hirao ...................................... 57/285 |
| 5,664,409 | * | 9/1997 | Lorenz .................................... 57/264 |
| 5,724,802 | * | 3/1998 | Foster ..................................... 57/290 |
| 5,802,832 | * | 9/1998 | Foster ..................................... 57/264 |

FOREIGN PATENT DOCUMENTS 2-175937   7/1990   (JP) .

* cited by examiner

*Primary Examiner*—John J. Calvert
*Assistant Examiner*—Shawn R Hurley
(74) *Attorney, Agent, or Firm*—Armstrong, Westerman, Hattori, McLeland, & Naughton, LLP (57) ABSTRACT

By appropriately controlling a yarn tension of an upstream side from a false twist device, variations in yarn quality among packages can be eliminated. A false twist texturing unit 7 which imparts a yarn Y with a false twist, a first feed roller 4 arranged in the upstream side from the false twist texturing unit 7, and an upstream side yarn tension control device 30 which automatically adjusts the rotation speed of a first feed roller 4 such that the upstream side yarn tension T1 is maintained within a fixed range are provided. A downstream side yarn tension control device 35 which automatically adjusts the false twist device 7 such that downstream side yarn tension T2 is maintained within a fixed range is also provided. Additionally, a determining unit 45 which determines whether or not the yarn quality is satisfactory based on the detection result of an upstream side yarn tension detecting unit 24 and a downstream side yarn tension detection unit 35 is also provided.

15 Claims, 7 Drawing Sheets

FALSE TWIST TEXTURING MACHINE

FIELD OF THE INVENTION

The present invention relates to a false twist texturing machine which imparts a false twist in a filament yarn through a friction of a rotating member like a nip twister or a friction disk, producing a crimped processed yarn.

BACKGROUND OF THE INVENTION

A conventional false twist texturing machine is provided with a plurality of false twist texturing units, and false twisting is carried out by passing the yarn along as it is false twisted by the false twist texturing units. A false twist texturing unit in such a conventional false twist texturing machine looks like the example shown FIG. 4. This conventional false twist texturing machine is comprised of a plurality of false twist texturing units 1 arranged in a row perpendicular to the plane of the page. Each false twist texturing unit 1 is provided with a first feed roller 4 which draws the yarn Y (filament yarn) from out a supply package 3 held in a creel stand 2. In the conventional false twist texturing machine, the first feed roller 4 is arranged such that it receives driving force from a line shaft shared by all false twist texturing units 1, and all the false twist texturing units are driven at a common rotary speed.

Figure 4:
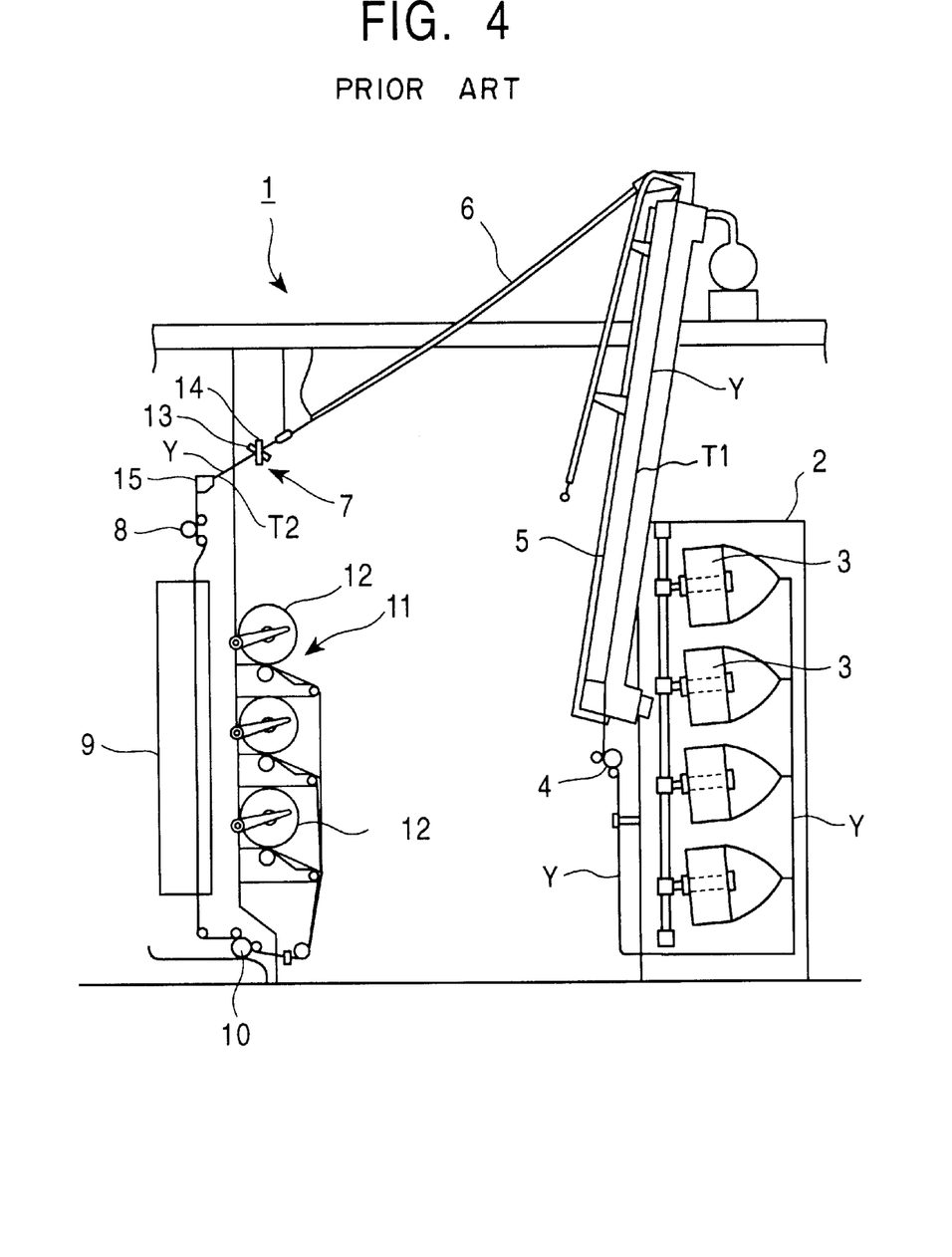
FIG. 4 is a diagram showing a conventional false twist texturing unit.

A yarn Y, which passes in sequence from the first feed roller 4 to a first heater 5 and to a cooling plate 6 is imparted with a false twist by a false twist device 7 (a nip twister). The yarn Y imparted with the false twist then passes sequentially through a yarn tension detection unit 15, a second feed roller 8, a second heater 9 and a third feed roller 10. It is then wound into a package 12 by a winding device 11, completing the false twist texturing process.

Figure 5:
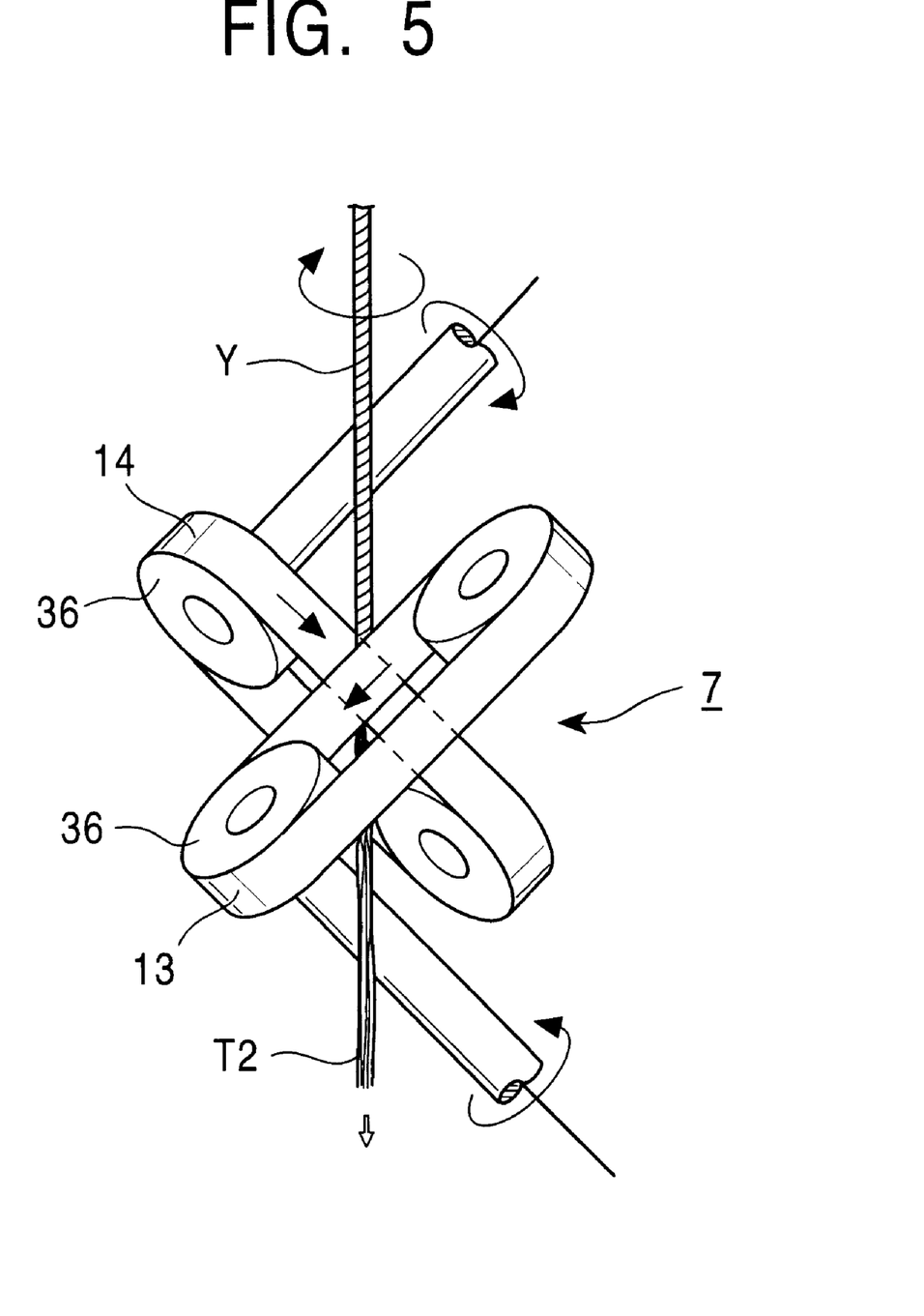
FIG. 5 is a perspective illustration showing a principle of a false twist created by a nip-twister.

The false twist device, that is, nip twister 7, as shown in the enlarged view of FIG. 5, is provided with a pair of crossed belts 13, 14 which nips the yarn Y, propelling and twisting the yarn Y. The twist created by the nip twister 7 is transmitted as far as the first feed rollers 4 and is heat-set by first heater 5. In other words, the nip twister 7 causes the upstream side to become the twisted side and the downstream side to become the untwisted side.

Thus, the belt-type nip twister 7 is arranged such that it nips the yarn Y using two endless belts that are crossed in contact with each other. By rotationally driving each belt, the yarn Y can be passed along and twisted. Both the nip pressure (contact pressure) of the belts and the rotational speed (the belt surface speed) affect the yarn tension T2 of the downstream (untwisted) side. The tension T2 of the untwisted yarn Y, in turn, affects the quality and characteristics of the yarn Y after it is untwisted. Additionally, changes in the running time of the belt also alter the tension T2 of the untwisted yarn Y, even if the nip pressure and rotational speed remain constant.

Normally, by adjusting the nip pressure and maintaining the constant tension T2 of the untwisted yarn Y2, the quality and characteristics of the yarn Y are kept constant. Specifically, as shown in FIG. 4, the yarn tension detection unit 15 for detecting the tension T2 of the untwisted yarn Y is provided on the downstream side from the belt type nip twister 7 to constantly monitor the tension T2 of the untwisted yarn Y. To control the tension T2 of the untwisted yarn Y, a target tension is pre-set and the detected tension T2 of the untwisted yarn Y is compared against the target value. If the detected value differs from the target value, the nip pressure of belts 13 and 14 are adjusted based on the disparity. When the nip pressure of the belts 13, 14 is adjusted, the tension T2 of the untwisted yarn on the downstream side is altered. Thus, it is possible to have the detected tension value approximate the target value.

There is variation, however, in the yarn quality of the packages 12 produced among the different false twist texturing units 1, as well as within the packages 12 of the same unit 1, in the conventional false twist texturing machine. The causes of this variation are mainly the mechanical or yarn supply-related problems. The mechanical causes are yarn slippage at the feed rollers 4 and positional differences between the upper and lower levels of the supply packages 3 in the creel stand 2. The supply-related cause is that there is variation in the degree of elongation of the individual yarns supplied to the false twist texturing units 1. This variation occurs when different supply packages 3 are used, or as the yarn is taken off the same supply packages 3.

When there is variation in the condition of the supply side yarn due to such mechanical or supply-related problems, the tension T1 of the yarn between the first feed roller 4 and the false twist device 7 (tension of the twisted side) changes, and thus variation of the tension T1 between the false twist texturing units 1 arises even if the yarn is drawn at a constant draw rate (the ratio of the surface speed of the second feed roller 8 to that of the first feed roller 4) at the false twist texturing units 1. As a result, the yarn quality varies between each false twist texturing unit 1, and further, varies within each wound package 12. This occurs even with conventional control systems that keep the tension of the untwisted yarn T2 constant.

SUMMARY OF THE INVENTION

In order to eliminate these problems and improve the conventional technology, it is an object of the present invention to provide a false twist texturing machine which can eliminate the variations in yarn quality between wound packages.

The means employed by the present invention to appropriately control a yarn tension in an upstream side from a false twist device is a false twist texturing machine comprised of a false twist device for imparting the yarn with a false twist, a first feed roller arranged on the upstream side from the false twist device, and a yarn tension control device for automatically controlling the rotation speed of the first feed roller relative to the yarn tension of the upstream side.

Thus, since the false twist texturing machine of the present invention controls the speed of the first feed roller in relation to the yarn tension of the upstream side from the false twist device, the yarn tension of the upstream side can be appropriately controlled, and variations in the yarn quality of the wound packages can be eliminated.

Specifically, either an upstream side yarn tension control device that automatically controls the rotation speed of the first feed roller such that the yarn tension of the upstream side from the false twist device is maintained within a fixed range, or a yarn tension ratio control device which automatically controls the rotation speed of the first feed roller such that the ratio of the yarn tension of the upstream side from the false twist device to the yarn tension of the downstream side from the false twist device is maintained within a fixed range may be employed as the yarn tension control device.

The means employed by the present invention to maintain an appropriate tolerance range for the draw rate of the yarn is a false twist texturing machine in which an upstream side yarn tension control device can set an upper limit and a lower limit within which the rotation speed of the first feed roller can change.

Consequently, in the false twist texturing machine of the present invention, the ratio of the speed (draw rate) of the second feed roller arranged on the downstream side from the false twist device of the first feed roller is appropriately adjusted within a permitted range, and variations in the yarn quality of the packages are eliminated.

Specifically, the upstream side yarn tension control device which automatically controls the rotation speed of the first feed roller such that the yarn tension of the upstream side from the false twist device is maintained within a fixed range, or a yarn tension control device which automatically controls the rotation speed of the first feed roller such that the ratio of the yarn tension of the upstream side from the false twist device to the yarn tension of the downstream side from the false twist device is maintained within a fixed range may be employed as the yarn tension control device.

The means employed by the present invention to appropriately control the yarn tension of both the upstream side and the downstream side from the false twist device is a false twist texturing machine provided with a downstream side yarn tension control device that automatically controls the false twist device such that the yarn tension of the downstream side from the false twist device is maintained within a fixed range. Further, when the false twist device operates on a plurality of control objects, each of the control objects is controlled by the downstream side yarn tension control device, and automatically controlled such that the yarn tension is maintained within a fixed range. For example, in the case where the false twisting device is a belt-style nip twister that nips, twists and propels the yarn where the belts cross, the nip pressure between the belts and/or the rotation speed of the pair of belts can be controlled by the downstream side yarn tension control device.

Consequently, in the false twist texturing machine of the present invention, since the yarn tension or yarn tension ratio of the upstream side from the false twist device is controlled by adjusting the speed of the first feed roller, and since the yarn tension of the downstream side from the false twist device is appropriately controlled by the downstream side yarn tension control device, variations in the yarn quality of the packages can be eliminated.

The means employed by the present invention to appropriately control the yarn tension of the upstream side from each false twist device and eliminate variation in the yarn quality between the false twist texturing units when a plurality of false twist texturing units are provided is the false twist texturing machine comprising a plurality of false twist devices for imparting the false twists to the yarn at each of the false twist texturing units, the first feed rollers arranged in the upstream side of each of the false twist devices, and the upstream side yarn tension control devices for automatically controlling the individual rotation speed of each first feed roller relative to the yarn tension of its corresponding upstream side from each false twist device.

Thus in the false twist texturing machine of the present invention, the yarn tension of the upstream side is appropriately controlled by controlling either the yarn tension of the upstream side from the false twist texturing unit, or the yarn tension ratio of the upstream side yarn tension to the downstream side yarn tension by adjusting the speed of the first feed roller of each false twist texturing unit. Consequently, variations in yarn quality of the wound packages between false twist texturing units can be eliminated.

The means employed by the present invention to enable the detection of yarn tension of the upstream side from the false twist device and to enable the twist formed by the false twist device to be spread as far as the upstream side of the heater, and then to be reliably heat-set by the heater is the false twist texturing machine comprising the false twist device that imparts the false twist to the yarn, the heater arranged in the upstream side from the false twist device, the first feed roller arranged in the upstream side from the heater, and a yarn tension detection unit for detecting the yarn tension between the heater and the first feed roller.

Thus, in the false twist texturing machine of the present invention, the yarn quality of each wound package can be controlled by detecting the yarn tension of the upstream side from the false twist device while the yarn is in a state that allows the twist to be reliably heat-set by the heater.

The means employed by the present invention to enable determination of whether or not the yarn quality is satisfactory is the false twist texturing machine comprised of an upstream side yarn tension detection unit for detecting the yarn tension of the upstream side from the false twist device, a downstream side yarn tension detection unit for detecting the yarn tension of the downstream side from the false twist device, and a determining unit for determining whether or not the yarn quality is satisfactory based on the detection results of the upstream side yarn tension detection unit and the downstream side yarn tension detection unit.

Thus, in the false twist texturing machine of the present invention, since the yarn quality can be determined based upon the upstream side and downstream side yarn tension detection results, greater management of yarn quality is enabled.

The means employed by the present invention to enable detection of whether or not the yarn quality is satisfactory while the yarn tension of the downstream side (untwisted side) is being appropriately controlled is the false twist texturing machine provided with the downstream side yarn tension control device which controls the yarn tension such that the yarn tension of the downstream side from the false twist device is maintained within a fixed range.

Thus, in the false twist texturing machine of the present invention, since the yarn quality can be determined based upon the upstream side and downstream side yarn tension detection results while the tension of the untwisted yarn is being appropriately controlled, the greater management of yarn quality is enabled.

The means employed by the present invention to enable detection of whether or not the yarn quality is satisfactory while the yarn tension of the downstream side (untwisted side) and the upstream side (twisted side) is being appropriately controlled is the false twist texturing machine provided with the upstream side yarn tension control means for controlling yarn tension such that the yarn tension of the upstream side from the false twist device is maintained within a fixed range.

Thus, in the false twist texturing device of the present invention, since the yarn quality can be determined based upon the detected upstream side and downstream side yarn tensions while the upstream side and downstream side yarn tension is being appropriately controlled, even the greater management of yarn quality is enabled. Moreover, the yarn tension of the upstream side from the false twist device indicates the yarn tension between the first feed roller and the false twist device, and the yarn tension of the downstream side from the false twist device indicates the yarn tension between the false twist device and the second feed roller.

DETAILED DESCRIPTION OF THE PREFERRED EMBODIMENTS

The false twist texturing machine that is the object of the present invention comprises, sequentially from the yarn supply side, a first feed roller for feeding the yarn, a heater for applying heat to the yarn, a false twist texturing unit for imparting the yarn with a false twist, a second feed roller for feeding the yarn and a yarn winding device for winding the yarn. As the yarn is drawn between the first and second feed rollers, the yarn is textured with a false twist through the operation of the heater and the false twist device. As needed, a second heater and a third feed roller can be provided between the second feed roller and the winding device.

Figure 1:
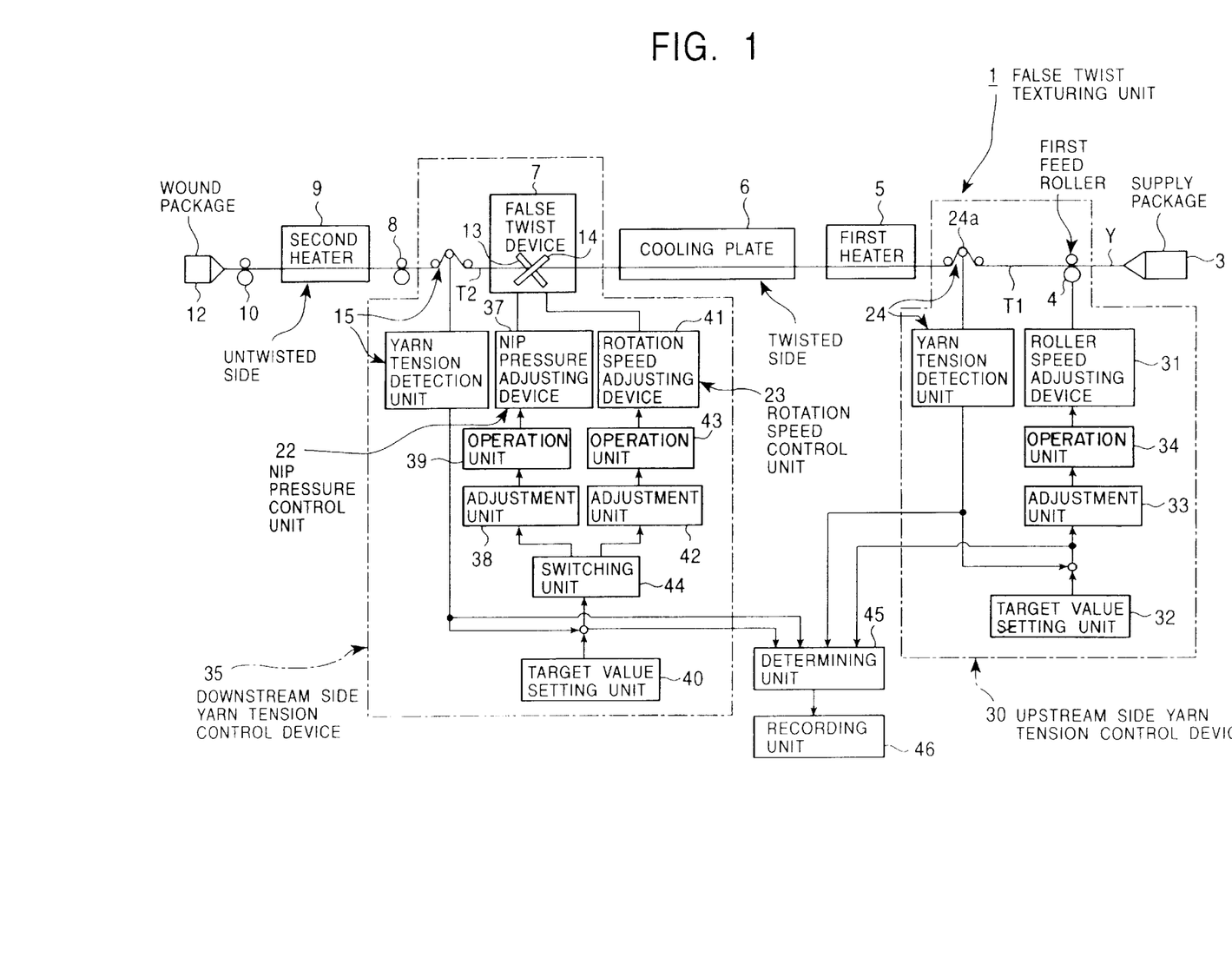
FIG. 1 is a typical control block diagram showing a yarn path in one false twist texturing unit of a first embodiment of a false twist texturing machine according to the present invention.
Figure 2A:
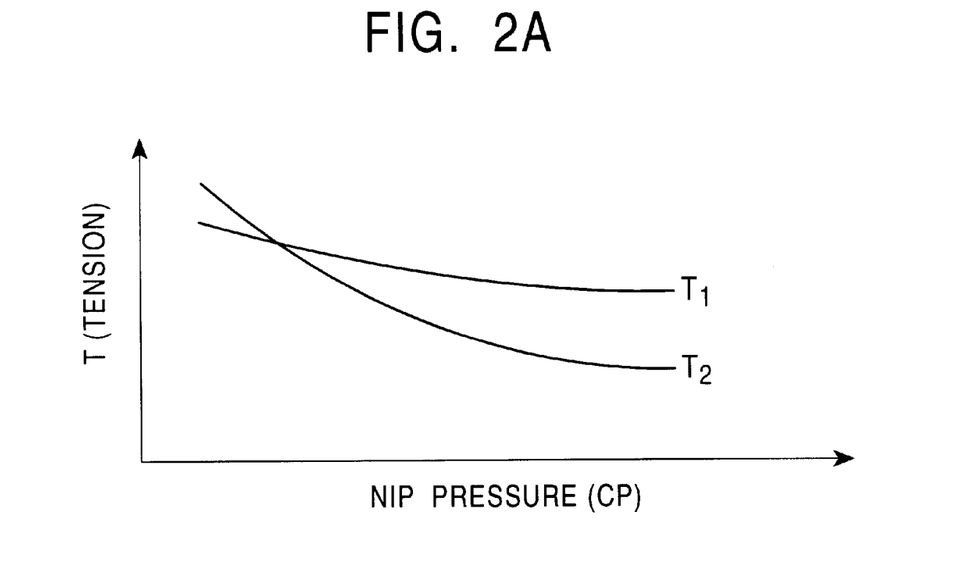
FIG. 2A is a diagram showing the characteristic relationship between twisted yarn tension and nip pressure of a nip twister in a false twist texturing machine according to the present invention.
Figure 2B:
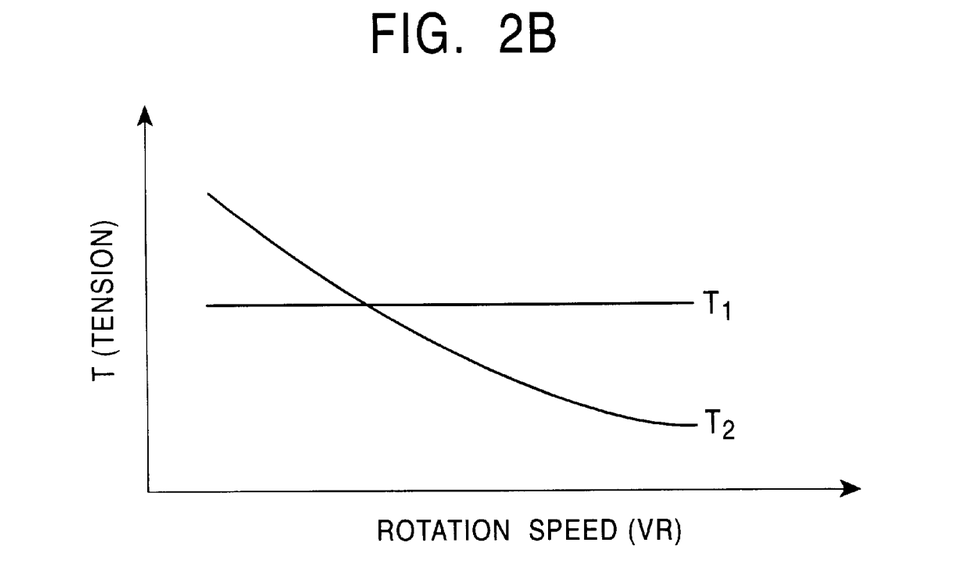
FIG. 2B is a diagram showing the characteristic relationship between untwisted yarn tension and rotation speed of a nip twister in a false twist texturing machine according to the present invention.

The structure of the present invention will now be explained based upon the embodiment depicted in the accompanying diagrams. FIG. 1 and FIG. 2 show a first embodiment of the present invention. FIG. 1 is a typical control block diagram showing the yarn path in a false twist texturing unit of the present invention and FIG. 2 is a characteristic diagram showing the relationship between both the upstream side (twisted side) yarn tension T1 and the downstream side (untwisted side) yarn tension T2 and rotational speed, and nip pressure when a belt type nip twister is employed. The entire structure of the false twist texturing machine of the present embodiment is generally shown in FIG. 4.

The false twist-texturing machine is comprised of multiple rows of false twist texturing units 1 of the type shown in FIG. 1. Each false twist texturing unit 1 is provided with a first feed roller 4 which draws a yarn Y (synthetic filament yarn, in the present embodiment, partially oriented polyester yarn) from a supply package 3 held by a creel stand 2 (see FIG. 4). The yarn Y, which passes sequentially from first feed roller 4 to a yarn tension detection unit 24, to a first heater 5 and to a cooling plate 6, is given a false twist by a false twist texturing device 7 (a nip twister). Imparted with the false twist, the yarn Y is then passed sequentially to the yarn tension detection unit 15, a second feed roller 8, a second heater 9 and a third feed roller 10. It is then wound into a wound package 12 by a winding device 11 (see FIG. 4), and processing ends. Further, each false twist texturing unit 1 increases the speed of the second feed roller 8 relative to the first feed roller 4 at a fixed rate, thus drawing out the yarn Y at a speed that is in fixed proportion to that of the second feed roller 8. Thus, the yarn Y is false twisted as it is drawn out.

Each false twist texturing unit 1 of the false twist texturing machine is provided with an upstream side yarn tension control device 30 for controlling the yarn tension of the upstream side (twisted side) from the false twist device 7. The tension of the twisted yarn T1 is detected by the yarn tension detection unit 24 arranged such that the yarn tension of the upstream side from the false twist texturing unit 7 is detected. The upstream side yarn tension control is performed based on this detection result. The upstream side yarn tension control device 30 is comprised of the yarn tension detection unit 24, a roller speed adjusting device 31 for adjusting the rotation speed of the first feed roller 4, a target value setting unit 32 for setting the target tension of the upstream side yarn Y, and an adjustment unit 33 and an operation unit 34 for controlling the roller speed adjusting device 31 based on the disparity between the detection result of the yarn tension detection unit 24 and the target value. The yarn tension detection unit 24 is comprised of a detection roller 24a which receives the tension of yarn Y, and a detection tool (not shown in the drawing) comprised of a load cell, or the like for detecting the tension received. By positioning the detection roller 24a between the first heater 5 and the first feed roller 4, the twist formed by the false twist device 7 is allowed to spread to the upstream side of the first heater 5 without being impeded by the yarn tension detection unit 24, thus allowing reliable heat-setting. Moreover, when the twist is enabled to spread and pass through the detection roller 24a, it is also possible to position the detection roller 24a between the false twist texturing unit 7 and the cooling plate 6, or between the false twist texturing unit 7 and the first heater 5.

The roller speed adjusting device 31 may employ a variable speed motor which drives the first feed roller 4, a clutch capable of adjusting speeds (for example, an eddy-current type clutch) which connects the first feed roller 4 with a line shaft (not shown in the drawing) used commonly by each of the false twist texturing units 1, or the like. This allows the first feed roller 4 to rotate independently within each false twist texturing unit 1. The target value setting unit 32 defines the upper and lower limits of the upstream side yarn tension value T1 such that yarn tension is maintained within an appropriate target range. Additionally, the target value setting unit 32 can be set such that it defines the upper and lower limits of the control range to enable adjustment of the rotation speed of the first feed roller 4 centering the target speed around a speed set as the yarn processing speed in each of the false twist texturing units 1. This enables the yarn draw ratio to be maintained within a fixed range.

Figure 3:
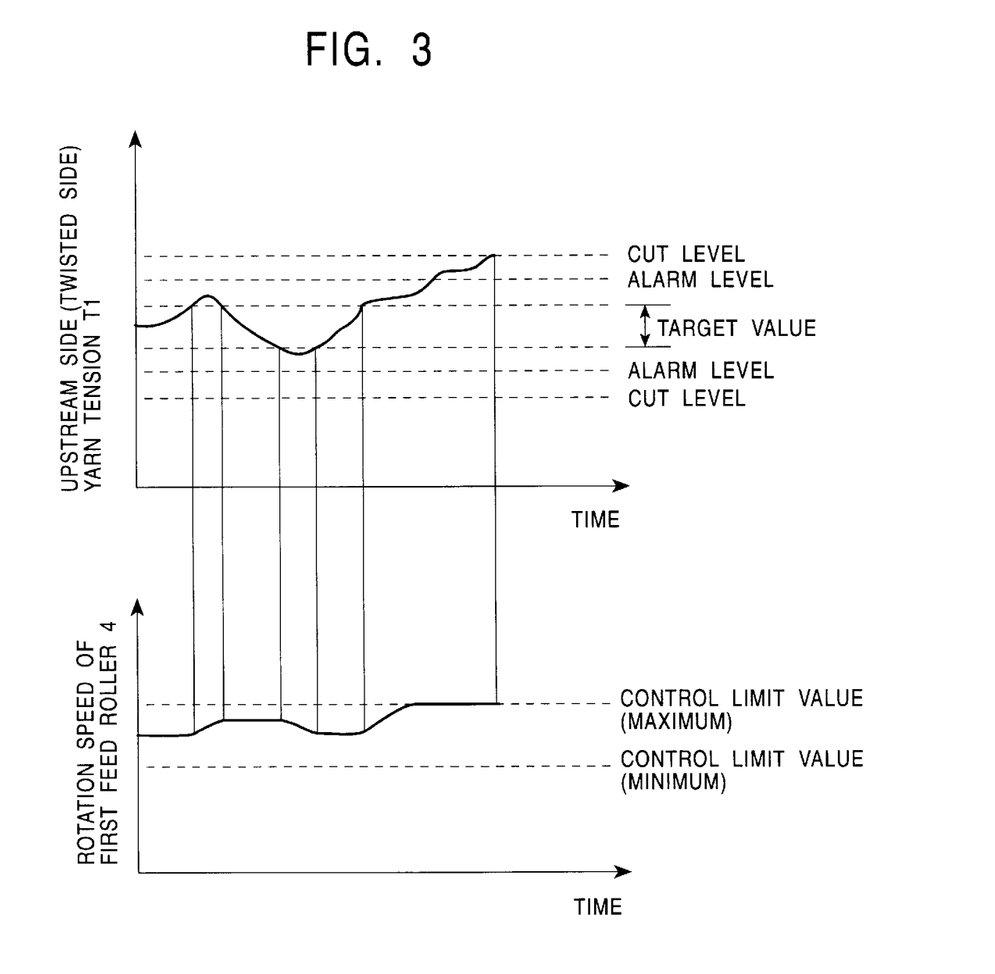
FIG. 3 is graph showing the relationship between the rotation speed of the first front roller 4 and changes in upstream (twisted side) yarn tension T1.

The adjustment unit 33 and the operation unit 34 are set to control the roller speed adjusting device 31 such that the rotation speed of the first feed roller 4 is controlled as described below. In other words, as shown in FIG. 3, while the disparity is within the target range, the rotation speed of the first feed roller 4 is maintained, but when the disparity exceeds the target range, the rotation speed of the first feed roller 4 is adjusted such that the disparity returns to the target range. Moreover, since the upper and lower control limit values of the rotation speed of the first feed roller 4 are set, when the upstream side yarn tension T1 still does not fall back within the target range even after changing the rotation speed of the first feed roller 4, the rotation speed of the first feed roller 4 can be brought to the upper or lower limits, but not exceeded. The adjustment unit 33 and the operation unit 34 may also be arranged such that they sequentially control the roller speed adjustment device 31 based on the amount of disparity between the target value and the detection result of the yarn tension detection unit 24. The second feed roller 8, which sets the yarn speed, is rotated at a fixed rotation speed.

Further, the false twist texturing machine is provided with a downstream side yarn tension control device 35 for controlling the yarn tension of the downstream side (untwisted side) from the false twist device 7 inside each false twist texturing unit 1. The downstream side yarn tension control device 35 is provided with a nip pressure control unit 22 for controlling the nip pressure of the false twist device 7 comprised of belt type nip twisters, and a rotation speed control unit 23 for controlling the rotation speed of the false twist device 7. The nip pressure control and rotation speed control are performed based upon detection of the untwisted yarn tension T2 by the yarn tension detection unit 15 arranged such that the yarn tension of the downstream side from the nip twisters 7 is detected. Further, since the nip pressure is generated by one of the belts 13, 14 (see FIG. 5) exerting the pressure against the other through a pneumatic cylinder (not shown in the drawing), the nip pressure control can be varied by adjusting the pressure exerted by the pneumatic cylinder. Additionally, since the pair of belts 13, 14 of the nip twister 7 are driven by being wound around a driving pulley 36 (see FIG. 5) of the motor (not shown in the drawing), the rotation speed can be adjusted by directly controlling the rotation speed of the motor.

The principle behind this nip pressure control and the rotation speed control is made apparent by the characteristic diagrams shown in FIG. 2A and FIG. 2B. These diagrams indicate a high degree of correlation between the nip pressure (CP) and the untwisted yarn tension T2, and a roughly direct correlation between the rotation speed (VR) of the nip twister 7 and the untwisted yarn tension T2. In other words, by adjusting the nip pressure (CP) and/or the rotation speed (VR) based on these functions, the untwisted yarn tension T2 can be controlled such that it is brought to the target value.

The nip pressure control unit 22, as shown in FIG. 1, is comprised of the downstream side yarn tension detection unit 15, a nip pressure adjusting device 37 comprising a hydraulic cylinder for adjusting the nip pressure (CP), a target value setting unit 40 for setting the yarn tension of the downstream side, and an adjustment unit 38 and an operating unit 39 for operating the nip pressure adjusting device 37 based on the disparity between the target value and the value detected by the yarn tension detection unit 15. The operating unit 39 supplies a desired pneumatic pressure to the nip pressure adjusting device 37 comprised of a pneumatic cylinder which controls the nip pressure (CP) between the belt 13 and the belt 14.

The rotation speed control unit 23 is comprised of the downstream side yarn tension detection unit 15, a rotation speed adjusting device 41 comprised of a variable speed motor which adjusts the rotation speed (VR) of the belts 13, 14 of the nip twister 7, the target value setting unit 40 for setting the yarn tension of the downstream side, an adjustment unit 42 and operating unit 43 for operating the rotation speed adjusting device 41 based upon disparity between the target value and the result detected by the yarn tension detection unit 15.

Since the yarn tension detection unit 15 and the target value setting unit 40 are shared, nip twister control unit 22 and the rotation speed control unit 23 are provided with a switching unit 44, and the output of the disparity between the value detected by the yarn detection unit 15 and the set value can be switched between the adjustment unit 38 of the nip control unit 22 and the adjustment unit 42 of the rotation speed control unit 23. The switching unit 44 is a circuit that can be arranged to either automatically switch the output destination of the disparity value at fixed intervals, or to allow manual switching of the output destination.

When the nip pressure (CP) is selected as the means to control the untwisted yarn tension T2 through the downstream side yarn tension control device 35, as shown in FIG. 2A, just a slight change in the twisted yarn tension T1 through control of the untwisted yarn tension T2 can influence the upstream side yarn tension control. In such case, a control period switching unit (not shown in the drawing) is provided such that when nip pressure (CP) is adjusted by the downstream side yarn tension control device 35, control is not performed simultaneously by the downstream side yarn tension control device 35 and the upstream side yarn tension control device 39, but rather in sequence. This control period switching unit can be arranged such that the period during which control is permitted is automatically changed at regular intervals, or is arbitrarily changed by a manual procedure.

Further, when rotation speed is selected as the means to control the tension T2 of the untwisted yarn through the downstream side yarn tension control device 35, as shown in FIG. 2B, the tension T1 of the twisted yarn may not change despite control of the untwisted yarn tension T2. In this case, a control period switching unit (not shown in the drawing) may be arranged such that the downstream side yarn tension control device 35 and the upstream side yarn tension control device 39 operate in parallel to control the yarn tension, or such that they operate in sequence. It should be noted that it is also possible to arrange the present invention such that only the nip pressure control unit or the rotation speed control unit are present.

As shown in FIG. 1, each false twist texturing unit 1 of the false twist texturing machine of the present embodiment is provided with a determining unit 45 and a recording unit 46 to enable management of the yarn tension. This management may be performed not only such that the twisted yarn tension T1 and the untwisted yarn tension T2 are controlled individually, but also such that they are controlled in concert. When they are controlled independently, the determining unit 45 determines whether or not the disparity between the target value of the twisted yarn tension T1 and the value detected by the yarn tension detection unit 24 is within a target range. It also determines whether or not the disparity between the target value of the untwisted yarn tension T2 and the value detected by the yarn tension detection unit 15 falls within a target range. Each determination is recorded in the recording unit 46. When control is performed collectively, determination of unsatisfactory yarn quality can be made when one of the disparity values falls outside the target range, and this result recorded . Thus, the false twist texturing machine of the present embodiment is able to determine whether or not the yarn quality in each false twist texturing unit is satisfactory, and enables greater management of each wound package 12.

Further, as shown in FIG. 3, an alarm level and a cut level may also be set for the determining unit 45. When the value detected by the yarn tension detection unit 24 exceeds a maximum or minimum alarm level, a warning may be generated, and a recording signal sent to the recording unit 46. Further, when the value detected by the yarn tension detection unit 24 exceeds a maximum or minimum cut level, an activation signal may be generated and sent to a cutting device (not shown in the drawing), forcing yarn Y passing through false twist texturing unit 1 to be cut. Similar alarm and cut levels may be set for the untwisted yarn tension T2.

In this way, the false twist texturing machine of the present embodiment controls, as necessary yarn tension such that the twisted yarn tension T1 of the upstream side from the nip twister 7 is maintained within a fixed range by altering the rotation speed of the first feed roller 4, and such that the untwisted yarn tension T2 of the downstream side from the nip twister 7 is maintained within a fixed range by altering the nip pressure (CP) and/or the rotation speed (VR) of the nip twister 7. In other words, the false twist texturing is performed while the twisted yarn tension T1 and the untwisted yarn tension T2 are being managed, resulting in processed yarn Y of superior quality. Moreover, such control is enabled for each false twist texturing unit, enabling the quality between each of the units to be maintained at a constant level.

Figure 6:
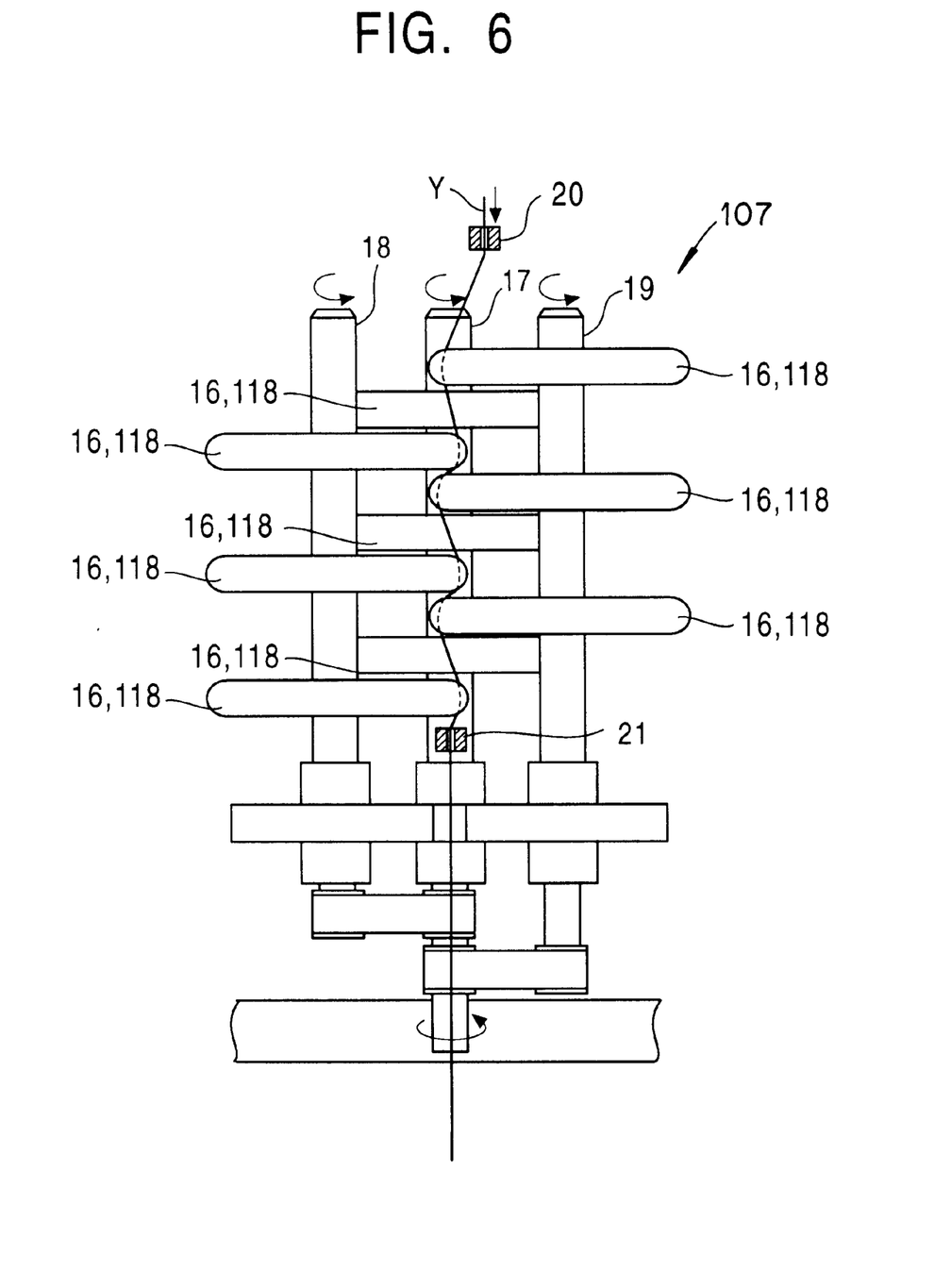
FIG. 6 is a cross sectional illustration showing a principle of a false twist created by a friction disk twister.

An alternate embodiment of the present invention, as shown in FIG. 6, may employ a friction disk type false twist device rather than a nip twister type device. The false twist device of this alternate embodiment is provided with three or more axles 17, 18, 19 comprising a plurality of individually integrated friction disks 16. Each friction disk 16 of an axle partially overlaps and crosses the plane of a friction disk of the other axles, and each friction disk 16 is arranged in parallel such that the plurality of disks 16 forms a spiral yarn path. The yarn Y is passed from a yarn guide 20, then run sequentially in a spiral by frictional contact through the overlapped, crossed portions of each of the friction disks 16, and passed to a downstream side yarn guide 21. Next, in a similar manner, as with the previously described false twist texturing unit shown in FIG. 4, the yarn is taken up into the wound package 12.

Each friction disk 16 rotates in the same direction, imparting the yarn Y with a twist. As is the case in the previously described embodiment, the twist in the upstream side (twisted side) from the friction disk grows with additional twists, while the twist in the downstream side (untwisted side) is released. Further, in order to manage the quality of the yarn, control such that the untwisted yarn tension of the downstream side from the friction disk is measured and maintained at a set value is performed in the same manner as with the nip twister. When the present invention is employed in a friction disk type false twist device, the plurality of control objects include the rotation speed of the friction disk, the distance between each of the axles, the pitch between the disks, and the like. Additionally, the number of disks and the disk diameters can also be adjusted.

Figure 7:
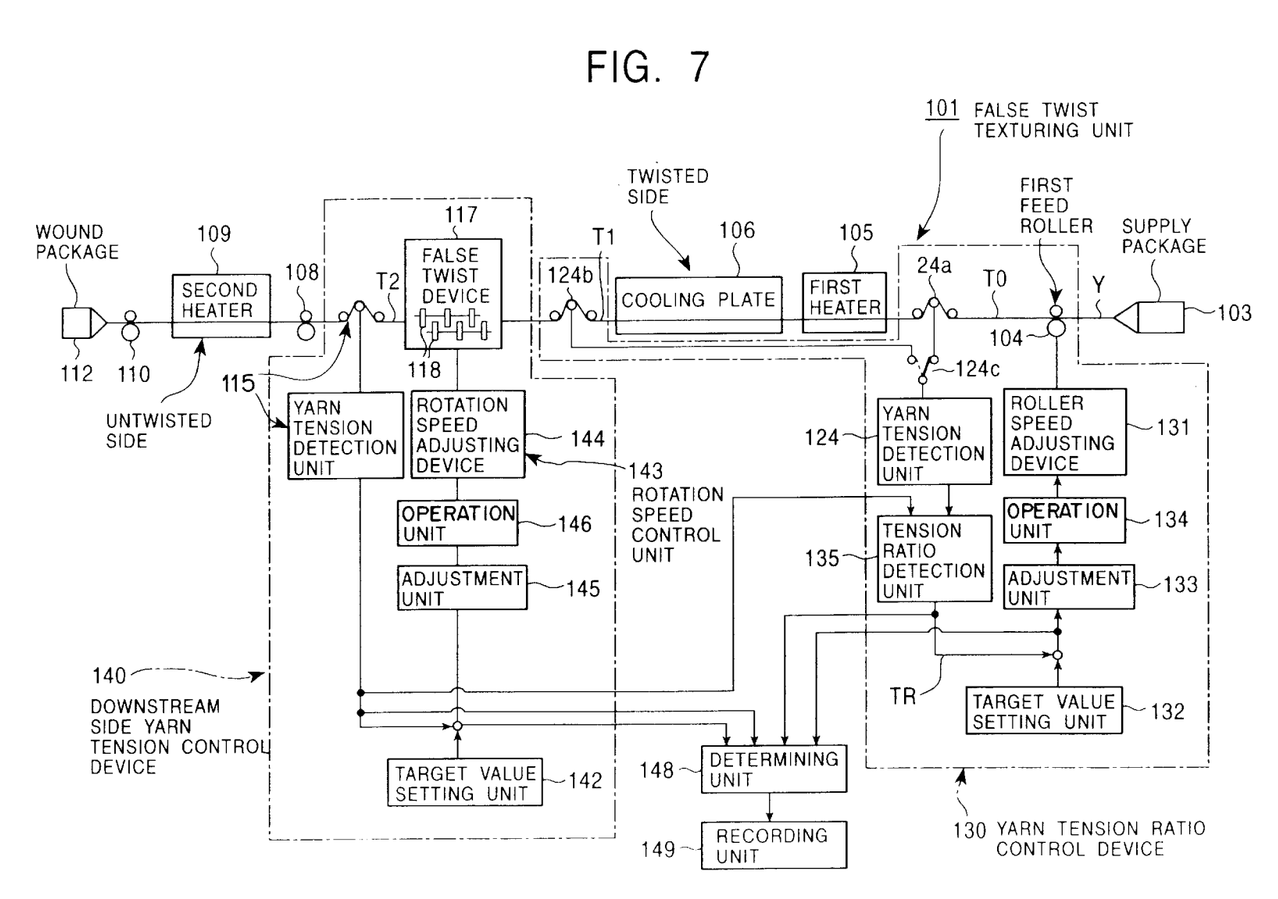
FIG. 7 is a typical control block diagram showing a yarn path in one of the false twist texturing units in a second embodiment of a false twist texturing machine according to the present invention.

FIG. 7 relates to the alternate embodiment of the present invention. FIG. 7 is an outline block diagram showing the yarn path in one of the false twist texturing units of the embodiment of the invention shown in FIG. 6. The entire structure of the false twist texturing machine of the present embodiment is generally the same as that of the first embodiment shown in FIG. 4.

The present embodiment, as shown in FIG. 7, is however comprised of false twist texturing units 101, a plurality of which are arranged parallel to each other. Each false twist texturing unit 101 is provided with a first feed roller 104 which draws a yarn Y (synthetic filament yarn: in the present embodiment, partially oriented polyester yarn) from a supply package 103 held by the creel stand 2 (see FIG. 4). The yarn, which passes sequentially from a first feed roller 104 to a detection roller 124a of a yarn tension detection unit 124, to a first heater 105, to a cooling plate 106, to a detection roller 124b, is given a false twist by a friction disk type twister 117 (see FIG. 6). The yarn Y imparted with the false twist, then passes sequentially to a yarn tension detection unit 115, a second feed roller 108, a second heater 109 and a third feed roller 110, and it is then wound into a wound package 112 by a winding device 11 (see FIG. 4), and processing ends. Further, each false twist texturing unit 1 increases the speed of the second feed roller 108 relative to the first feed roller 104 at a fixed rate, thus drawing out the yarn at a fixed rate between the first feed roller 104 and the second feed roller 8. Thus, yarn Y is false twisted as it is drawn out.

Each false twist texturing unit 1 of the false twist texturing machine is provided with a yarn tension ratio control device 130 for controlling the yarn tension ratio of the upstream side (twisted side) from the false twist device to the yarn tension of the downstream side from the false twist device. Control of the yarn tension ratio is carried out by detection of the tension of the twisted yarn T0 (also T1) by yarn tension detection unit 124, arranged such that the yarn tension of the upstream side from the false twist device 107 is detected, and by maintaining the yarn tension ratio TR of the upstream side yarn tension (T0 or T1) to the yarn tension T2 of the downstream side from the friction disk type twister 117 detected by the yarn tension detection unit 115 (TR= T0/T2 or T1/T2) within a fixed range. The yarn tension ratio control device 130 is comprised of the yarn tension detection unit 124, a roller speed adjustment device 131 for adjusting the rotation speed of the first feed roller 104, tension ratio detection unit 135 for determining the tension ratio TR (T0/T2 or T1/T2) from the results detected by the yarn tension detection unit 124 and the yarn tension detection unit 115, a target value setting unit 132 for setting the target tension ratio TR, and an adjustment unit 133 and an operating unit 134 for operating the roller speed adjustment device 131 based on the disparity between the tension ratio TR obtained from the tension ratio detection unit 135 and the set the target value.

The yarn tension detection unit 124 is comprised of detection rollers 124a, 124b which receive the tension of yarn Y, and a detection cell (not shown in the drawing) comprised of a load cell, or the like, for determining the received tension (T0 or T1). By positioning the detection roller 124a between the first heater 105 and the first feed roller 104, the twist formed by the false twist device 107 is allowed to spread upstream of first heater 105 without being impeded by the yarn tension detection unit 124, thus permitting reliable heat-setting. When the twist spreads and passes the detection roller, the detection roller is placed between the false twist device 107 and the cooling plate 106 or the false twist device 107 and the first heater 105. In order to switch between either detection of the yarn tension T0 of the upstream side from the first heater 105 and detection of the yarn tension T1 of the downstream side from the first heater 105, the yarn tension detection unit 124 can be provided with a switching unit 124c. It is also possible to provide only one of the detection rollers 124a, 124b and not the other.

The roller speed changing device 131 may employ either a variable speed motor which drives the first feed roller 104, a clutch, or the like, capable of adjusting speeds (for example, an eddy-current type clutch) which connects the first feed roller 104 with a line shaft (not shown in the drawing) used commonly by each of the false twist texturing units 101. This allows the first feed roller 104 to rotate independently within each false twist texturing unit 101. The target value setting unit 132 defines the upper and lower limits of the tension ratio TR such that the yarn tension is maintained within an appropriate target range. Additionally, the target value setting unit 132 can be set such that it defines the upper and lower limits of the speed control range to enable adjustment of the rotation speed of the first feed roller 104, centering the target speed around a target speed set as the texturing speed in each of the false twist texturing units 101. This enables the yarn draw ratio to be maintained within a fixed range.

The first embodiment has been explained in reference to FIG. 3, but a second embodiment will now be explained, again using FIG. 3, but this time changing upstream yarn tension T1 to yarn tension ratio TR.

The adjustment unit 133 and the operation unit 134 are set to control the roller speed adjusting device 131 such that the rotation speed of the first feed roller 104 is controlled as described below. In other words, while the disparity is within a target range, the rotation speed of the first feed roller 104 is maintained, but when the disparity falls out of the target range, the rotation speed of the first feed roller 104 is adjusted such that the disparity returns to the target range. Further, since the upper and lower control limit values of the rotation speed of the first roller 104 are set, when the tension ratio TR still does not fall back within the target range even after adjusting the rotation speed of the first roller 104, the rotation speed of the first feed roller 104 is brought to the upper or lower limit, but not further adjusted. The adjustment unit 133 and the control unit 134 are also arranged such that they sequentially control the roller speed changing device 131 based on the amount of disparity between the target value and the detected tension ratio TR value when the disparity is within a target value.

Further, as shown in FIG. 7, the false twist texturing machine of the present embodiment is provided with the downstream side yarn tension control device 140 for controlling the yarn tension of the downstream side (untwisted side) from the friction disk type twister 117 inside each false twist texturing unit 101. The downstream side yarn tension control device 140 is provided with a rotation speed control unit 143 for the friction disk type twister 117 employing friction disks (see the friction disks 118 shown in FIG. 6). Rotation speed control involves detection of the untwisted yarn tension T2 by the yarn tension detection unit 115 arranged such that the yarn tension of the downstream side from the friction disk type twister 117 is determined, and control of the rotation speed of the friction disks 118 based on this determination.

The rotation speed control unit 143 is comprised of the downstream side yarn tension detection unit 115, the rotation speed adjusting device 144 comprised of a variable speed motor which adjusts the rotation speed (VR) of the friction disks 118, 118 . . . 118, the target value setting unit 142 for setting the target yarn tension of the downstream side, the adjustment unit 145 and the operating unit 146 for operating the rotation speed adjusting device 144 based on the disparity between the target value and the value detected by the yarn tension detection unit 115.

As shown in FIG. 7, each false twist texturing unit 101 of the false twist texturing machine of the present embodiment is provided with a determining unit 148 and a recording unit 149 to enable management of the yarn tension. This management may be performed not only by controlling the twisted yarn tension T0 (or T1) and the untwisted yarn tension T2 individually, but also by controlling them in concert. When they are controlled independently, the determining unit 148 determines whether or not the disparity between the target tension ratio TR and the detected value falls within a target range. It also determines whether or not the disparity between the target value of the untwisted yarn tension T2 and the value detected by yarn tension detecting unit 115 falls within a target range. These determination results are recorded in the recording unit 149. When the control is performed collectively, determination of unsatisfactory yarn quality can be made when one of the disparity values falls outside the target range, and this result recorded. Thus, the false twist texturing machine of the present embodiment is able to determine whether or not the yarn quality in each false twist texturing unit is satisfactory, and enables greater management of each wound package 112.

Further, an alarm level and a cut level may also be set for the tension ratio TR in the determining unit 148. When the determined tension ratio TR rises above or falls below a maximum or minimum alarm level, a warning may be generated and a recording signal sent to the recording unit 149. Further, when the determined tension ratio TR exceeds a maximum or minimum cut level, an activation signal may be generated and sent to a cutting device (not shown in the drawing), the forcing yarn Y passing through the false twist texturing unit 101 to be cut. Similar alarm and cut levels may be set for the twisted yarn tension T0 (T1) and/or the untwisted yarn tension T2.

In this way, the false twist texturing machine of the present embodiment controls the yarn tension such that the tension ratio TR of the twisted yarn tension T0 (or T1) of the upstream side from the friction disk type twister 117 and the untwisted yarn tension T2 of the downstream side is controlled within a fixed range by adjusting the rotation speed of the first feed roller 104, and such that the untwisted yarn tension T2 of the downstream side from the friction disk type twister 117 is controlled within a fixed range by changing the rotation speed of the friction disks 118. In other words, false twist texturing is performed while the tension ratio TR and the untwisted yarn tension T2 are being managed, resulting in processed yarn Y of superior quality.

Moreover, such control is enabled for each false twist texturing unit, enabling the quality between each of the units to be maintained at a constant level. It should be further noted that a belt type nip twister as shown in FIG. 5 may be used in place of a friction disk type twister 117 employed in this second embodiment of the present invention.

In the false twist texturing machine of the present invention, by appropriately controlling the yarn tension of the upstream side from the false twist device, a superior processing method can be achieved wherein there is no variation in yarn quality among all yarn produced.

Further, in the false twist texturing machine of the present invention, by controlling the yarn tension of the upstream side from the false twist device of each false twist texturing unit, variations in yarn quality between each of the false twist texturing units can be eliminated, and a processing method wherein there is no variation in quality among all yarn produced can be achieved.

In the false twist texturing machine of the present invention, since yarn tension on the twisting side is detected while a twist is actually heat-set by the heater, the management of the yarn quality for all yarn produced is enabled.

Further, in the false twist texturing machine of the present invention, since it is determined whether or not the yarn quality is satisfactory based upon detected yarn tensions of the twisted and untwisted sides, the greater management of the yarn quality for all yarn produced is enabled.

Moreover, in the false twist texturing machine of the present invention, since it is determined whether or not the yarn quality is satisfactory based upon the detected yarn tension of the twisted and untwisted sides while the yarn tension of the untwisted side is being appropriately controlled, the greater management of the yarn quality for all yarn produced is enabled.

Further, in the false twist texturing machine of the present invention, since it is determined whether or not the yarn quality is satisfactory based upon the detected yarn tensions of the twisted and untwisted sides while the yarn is undergoing processing of superior quality than in conventional devices where only the untwisted yarn tension is controlled, the greater management of yarn quality for all yarn produced is enabled.

What is claimed is:

1. A false twist texturing machine comprising:
    a false twist device for imparting a yarn with a false twist;
    a first feed roller arranged in an upstream side from the false twist device;
    a second feed roller arranged at a downstream side of the false twist device;
    means for keeping the rotation speed of the second feed roller constant; and
    a yarn tension control device for automatically controlling the rotation speed of the first feed roller in relation to a yarn tension of the upstream side from the false twist device.

2. The false twist texturing machine as in claim 1 wherein the yarn tension control device is an upstream side yarn tension control device that senses yarn tension upstream of the false twist device and that automatically controls operation of the rotation speed of the first feed roller in response to the sensed varn tension such that the yarn tension on the upstream side of the false twist device is maintained within a fixed range.

3. The false twist texturing machine as in claim 2 wherein the upstream side yarn tension control device includes means to set an upper and lower control limit of a range within which the rotation speed of the first feed roller can change.

4. A false twist texturing machine comprising:

a false twist device for imparting yarn with a false twist;

a first feed roller arranged upstream from the false twist device;

an upstream side yarn tension control device that senses yarn tension upstream of the false twist device and that automatically controls rotation speed of the first feed roller in respect to the sensed yarn tension such that the yarn tension on the upstream side of the false twist device is maintained within a fixed range; and a downstream side yarn tension control device for automatically controlling operation of the false twist device such that yarn tension of the downstream side from the false twist device is maintained within a fixed range.

5. A false twist texturing machine comprising:

a false twist device for imparting a yarn with a false twist;

a first feed roller arranged upstream from the false twist device; and a yarn tension control device operative to automatically control the rotation speed of the first feed roller in response to yarn tension on the upstream side of the false twist device; and means for sensing yarn tension on the downstream side of said false twist device, wherein the yarn tension control device is a yarn tension control device that automatically controls the rotation speed of the first feed roller such that the ratio of the yarn tension on the upstream side of the false twist device to the yarn tension on the downstream side from the false twist device is maintained within a fixed range.

6. The false twist texturing machine as in claim 5 further comprising a downstream side yarn tension control device for automatically controlling operation of the false twist device such that yarn tension of the downstream side from the false twist device is maintained within a fixed range.

7. A false twist texturing machine comprising:

a plurality of false twist devices of a plurality of false twist texturing units to impart yarn with a false twist; and first feed rollers each arranged on an upstream side from each of the false twist devices of each false twist texturing unit such that the respective first feed rollers are independently rotatable.

8. The false twist texturing machine as in claim 7 further comprising a yarn tension control device in each of said false twist texturing units operative to automatically control the rotation speeds of the first feed roller of each false twist texturing unit in relation to the yarn tension on the upstream side of each of the false twist devices of the false twist texturing units.

9. A false twist texturing machine comprising:

a false twist texturing unit for imparting yarn with a false twist;

a heater arranged on an upstream side from the false twist device;

a first feed roller arranged on the upstream side of the heater; and a yarn tension detection unit operative to detect the yarn tension between the heater and the first feed roller.

10. A false twist texturing machine comprising:

an upstream side yarn tension detection unit operative to detect yarn tension on an upstream side of a false twist device;

a downstream side yarn tension detection unit operative to detect yarn tension on a downstream side of the false twist device; and a determining unit for determining whether or not the yarn quality is satisfactory based upon a comparison of the detected outputs of the upstream side yarn tension detection unit and the downstream side yarn tension detection unit.

11. The false twist texturing machine as in claim 10 including a downstream side yarn tension control device operative to control the yarn tension on the downstream side of the false twist device to maintain it within a fixed range.

12. The false twist texturing machine as in claim 11 including an upstream side yarn tension control device operative to control the yarn tension on the upstream side of the false twist device to maintain it within a fixed range.

13. A false twist texturing machine including a false twist device, a first feed roller arranged on an upstream side of the false twist device, a second feed roller arranged on a downstream side of the false twist device, and said false twist device being operative for imparting the yarn drawn between said first feed roller and said second feed roller with a false twist, wherein the second feed roller is rotated at a fixed rotation speed; and the rotation speed of the first feed roller is adjusted and controlled.

14. The false twist texturing machine as in any one of claims 4 through 13 wherein the false twist device comprises a plurality of individual friction disks integrated to a plurality of shafts, the friction disk of each shaft arranged such that it partially overlaps and crosses the plane of the friction disks of the other shafts, and wherein the yarn is frictionally passed in order through the crossed portions of the friction disks.

15. The false twist texturing machine as in any one of claims 4 through 13 wherein the false twist device imparts twist and transmission to yarn nipped between a pair of crossed rotating belts.

* * * * *